US012558473B2

(12) United States Patent
Saroha et al.

(10) Patent No.: US 12,558,473 B2
(45) Date of Patent: Feb. 24, 2026

(54) SYSTEMS, DEVICES, AND METHODS FOR ASPIRATING BIOLOGICAL MATERIAL FROM A BODY LUMEN

(71) Applicant: KONINKLIJKE PHILIPS N.V., Eindhoven (NL)

(72) Inventors: Princeton Saroha, Ladera Ranch, CA (US); Jeremy Stigall, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1306 days.

(21) Appl. No.: 17/276,345

(22) PCT Filed: Sep. 24, 2019

(86) PCT No.: PCT/EP2019/075579
§ 371 (c)(1),
(2) Date: Mar. 15, 2021

(87) PCT Pub. No.: WO2020/064660
PCT Pub. Date: Apr. 2, 2020

(65) Prior Publication Data
US 2022/0040394 A1     Feb. 10, 2022

Related U.S. Application Data

(60) Provisional application No. 62/738,691, filed on Sep. 28, 2018.

(51) Int. Cl.
*A61M 1/00*          (2006.01)

(52) U.S. Cl.
CPC .......... *A61M 1/743* (2021.05); *A61M 1/7413* (2021.05); *A61M 1/774* (2021.05);
(Continued)

(58) Field of Classification Search
CPC ........ A61M 1/743; A61M 1/774; A61M 1/81; A61M 1/82; A61M 1/7413; A61M 1/772;
(Continued)

(56) References Cited

U.S. PATENT DOCUMENTS

2006/0276743 A1* 12/2006 MacMahon ............. A61M 1/81
604/28
2011/0213297 A1     9/2011 Aklog
(Continued)

OTHER PUBLICATIONS

International Search Report and Written Opinion Dated Mar. 4, 2020 for International Application No. PCT/EP2019/075579 Filed Sep. 24, 2019.

*Primary Examiner* — Phillip A Gray

(57) ABSTRACT

An intraluminal system for aspirating biological material from a lumen of a patient includes a disposable intraluminal device having a proximal portion and a distal portion. The system includes a disposable pump configured to aspirate the biological material from the lumen of the patient. The disposable pump is coupled to the proximal portion of the intraluminal device. The disposable pump comprises a pump chassis that houses: an inlet port configured to sealably attach to the proximal portion of the intraluminal device; an outlet port configured to expel the aspirated biological from the pump; and a flow controller configured to adjust a fluid flow through the pump, wherein the pump chassis is sized and shaped to be manually supported by a user.

7 Claims, 9 Drawing Sheets

(52) U.S. Cl.
CPC ................ *A61M 1/81* (2021.05); *A61M 1/82* (2021.05); *A61M 1/772* (2021.05); *A61M 2205/058* (2013.01); *A61M 2205/273* (2013.01); *A61M 2205/3337* (2013.01); *A61M 2210/0693* (2013.01); *A61M 2210/1003* (2013.01); *A61M 2210/106* (2013.01); *A61M 2210/1064* (2013.01); *A61M 2210/1075* (2013.01); *A61M 2210/1082* (2013.01); *A61M 2210/12* (2013.01)

(58) Field of Classification Search
CPC ...... A61M 2205/058; A61M 2205/273; A61M 2205/3337
USPC ........................................................ 604/30
See application file for complete search history.

(56) References Cited

U.S. PATENT DOCUMENTS

| | | | |
|---|---|---|---|
| 2013/0281788 A1 | 10/2013 | Garrison | |
| 2013/0331805 A1* | 12/2013 | Brennan | ............... A61M 1/741 604/327 |
| 2015/0282821 A1 | 10/2015 | Look | |
| 2016/0097384 A1 | 4/2016 | Menjoh | |

\* cited by examiner

SYSTEMS, DEVICES, AND METHODS FOR ASPIRATING BIOLOGICAL MATERIAL FROM A BODY LUMEN

CROSS REFERENCE TO RELATED APPLICATIONS

This application is the U.S. National Phase application under 35 U.S.C. § 371 of International Application No. PCT/EP2019/075579 filed Sep. 24, 2019, which claims the benefit of U.S. Provisional Patent Application No. 62/738,691 filed Sep. 28, 2018. These applications are hereby incorporated by reference herein.

TECHNICAL FIELD

The present disclosure relates generally to pumping systems configured to aspirate biological material from a patient's lumen, such as a blood vessel. For example, a pumping system may include a handheld, disposable pump that includes an actuator and a pump chamber in communication with an intraluminal device inserted into the lumen of the patient.

BACKGROUND

Thrombectomy is commonly performed using a vacuum pump system, isolated from other treatments, in conjunction with a catheter. Aside from minimally invasive surgical intervention such as balloon angioplasty and various forms of atherectomy, other common methods include: open heart surgery and anticoagulation regimens. Existing pump systems often include reusable large footprint pumps that can be expensive to purchase and maintain, and difficult to sterilize for use with other patients.

Furthermore, some existing pump systems may lack power efficiency and/or consistent pump pressure due to the simplicity of the design. For example, an irregular pump vacuum cycle can produce periodic pressure spikes that, while short in duration, can be sufficiently high to cause a vessel to collapse.

SUMMARY

Embodiments of the present disclosure advantageously describe disposable pump systems and devices configured to aspirate biological material from a vessel of a patient. For example, in some embodiments, the disposable pump system comprises a pump chassis that is sized and shaped to be manually supported by a user. The pump chassis houses and/or couples to an inlet, pump chamber, a motor or actuator, and an outlet. The components of the pump and sized, shaped, and arranged to conserve size and weight and reduce cost while maintaining sufficiently high vacuum strength for use in aspiration thrombectomy.

In an exemplary aspect of the present disclosure, an intraluminal system for aspirating biological material from a lumen of a patient is provided. The system includes a disposable intraluminal device comprising a distal portion configured to be positioned within the lumen of the patient and a proximal portion in fluid communication with the distal portion and positioned outside of the patient; and a disposable pump configured to aspirate the biological material from the lumen of the patient, the disposable pump coupled to the proximal portion of the intraluminal device and comprising a pump chassis that houses: an inlet port configured to sealably attach to the proximal portion of the intraluminal device; an outlet port configured to expel the aspirated biological from the pump; and a flow controller configured to adjust the fluid flow through the pump, wherein the pump chassis is sized and shaped to be manually supported by a user.

In one aspect, the flow controller comprises a mechanical valve that is manually controllable by a user. In one aspect, the flow controller comprises an electronic flow control device. In one aspect, the pump chassis further houses a flow meter configured to detect a fluid flow through the pump and to provide an indication of the fluid flow. In one aspect, the flow meter comprises an electronic flow meter, and wherein the flow meter is in communication with the flow controller to provide feedback to the flow controller. In one aspect, the flow meter and flow controller are configured to operate in a proportional-integral-derivative arrangement. In one aspect, the flow controller is configured to repeatedly open and close to generate pulses of fluid pressure within the lumen of the patient. In one aspect, the pump chassis further houses: an actuator; a first pump chamber; a second pump chamber separate from the first pump chamber; and a dual displacement adapter coupled to the actuator such that the actuator is configured to drive the dual displacement adapter to pump fluid through each of the first pump chamber and the second pump chamber. In one aspect, the disposable intraluminal device comprises a fluid delivery lumen and an aspiration lumen separate from the fluid delivery lumen, and wherein the pump chassis further houses: a first pump chamber; a second pump chamber separate from the first pump chamber; a distal outlet in communication with the fluid delivery lumen of the disposable intraluminal device and the first pump chamber; and a distal inlet in communication with the aspiration lumen of the disposable intraluminal device and the second pump chamber, a proximal inlet in communication with the first pump chamber; and a proximal outlet in communication with the second pump chamber, wherein the pump is configured to pump a fluid from a fluid source coupled to the proximal inlet to the lumen of the patient through the first pump chamber, and wherein the pump is configured to aspirate the biological material from the lumen of the patient through the second pump chamber.

In an exemplary aspect of the present disclosure, an intraluminal system for aspirating biological material from a lumen of a patient is provided. The system includes a disposable intraluminal device comprising a distal portion configured to be positioned within the lumen of the patient and a proximal portion in fluid communication with the distal portion and positioned outside of the patient; and a pump chassis that houses: a first pump chamber; a second pump chamber separate from the first pump chamber; an actuator; and a dual displacement adapter coupled to the actuator such that the actuator is configured to drive the dual displacement adapter to pump fluid through each of the first pump chamber and the second pump chamber, wherein the pump chassis is configured to sealably attach to the proximal portion of the disposable intraluminal device, wherein the actuator is configured to drive the dual displacement adapter to aspirate the biological material through at least one of the first pump chamber or the second pump chamber, and wherein the actuator and dual displacement adapter are disposed within the pump chassis, and wherein the pump chassis is sized and shaped to be manually supported by a user.

In one aspect, the dual displacement adapter is configured to pump a fluid to the distal portion of the disposable intraluminal device through the first pump chamber, and to aspirate the biological material through the second pump chamber. In one aspect, the dual displacement adapter is configured to pump fluid through each of the first pump chamber and the second pump chamber in an alternating fashion. In one aspect, the dual displacement adapter comprises a cam coupled to a first piston in communication with the first pump chamber and a second piston in communication with the second pump chamber. In one aspect, the dual displacement adapter comprises a plurality of gears configured to distribute torque from the actuator to a first pump member in communication with the first pump chamber and a second pump member in communication with the second pump chamber.

In an exemplary aspect of the present disclosure, an intraluminal system for aspirating biological material from a lumen of a patient is provided. The system includes a disposable intraluminal device comprising a distal portion configured to be positioned within the lumen of the patient and a proximal portion in fluid communication with the distal portion and positioned outside of the patient, wherein the disposable intraluminal device comprises a fluid delivery lumen and an aspiration lumen separate from the fluid delivery lumen; and a disposable pump configured to deliver a fluid to the lumen of the patient and aspirate the biological material from the lumen of the patient, the disposable pump coupled to the proximal portion of the intraluminal device and comprising a pump chassis that houses: a first pump chamber and a second pump chamber separate from the first pump chamber; a distal outlet in communication with the fluid delivery lumen of the disposable intraluminal device and the first pump chamber; and a distal inlet in communication with the aspiration lumen of the disposable intraluminal device and the second pump chamber, a proximal inlet in communication with the first pump chamber; and a proximal outlet in communication with the second pump chamber; wherein the pump is configured to pump a fluid from a fluid source coupled to the proximal inlet to the lumen of the patient through the first pump chamber, wherein the pump is configured to aspirate the biological material from the lumen of the patient through the second pump chamber, and wherein the pump chassis is sized and shaped to be manually supported by a user.

In one aspect, the proximal inlet is in communication with the proximal outlet to recycle aspirated fluid from the second pump chamber to the lumen of the patient through the first pump chamber. In one aspect, the system further comprises a filter disposed between the proximal outlet and the proximal inlet. In one aspect, the proximal inlet is in communication with a fluid reservoir, and wherein the proximal outlet is in communication with a waste receptacle separate from the fluid reservoir. In one aspect, the disposable intraluminal device comprises a sheath surrounding the fluid delivery lumen, wherein the aspiration lumen is coaxially disposed within the fluid delivery lumen, and wherein a distal tip of the sheath includes a narrowing taper. In one aspect, the disposable intraluminal device comprises a sheath surrounding the fluid delivery lumen, wherein the aspiration lumen is coaxially disposed within the fluid delivery lumen, and wherein a distal tip of the sheath includes a widening taper.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
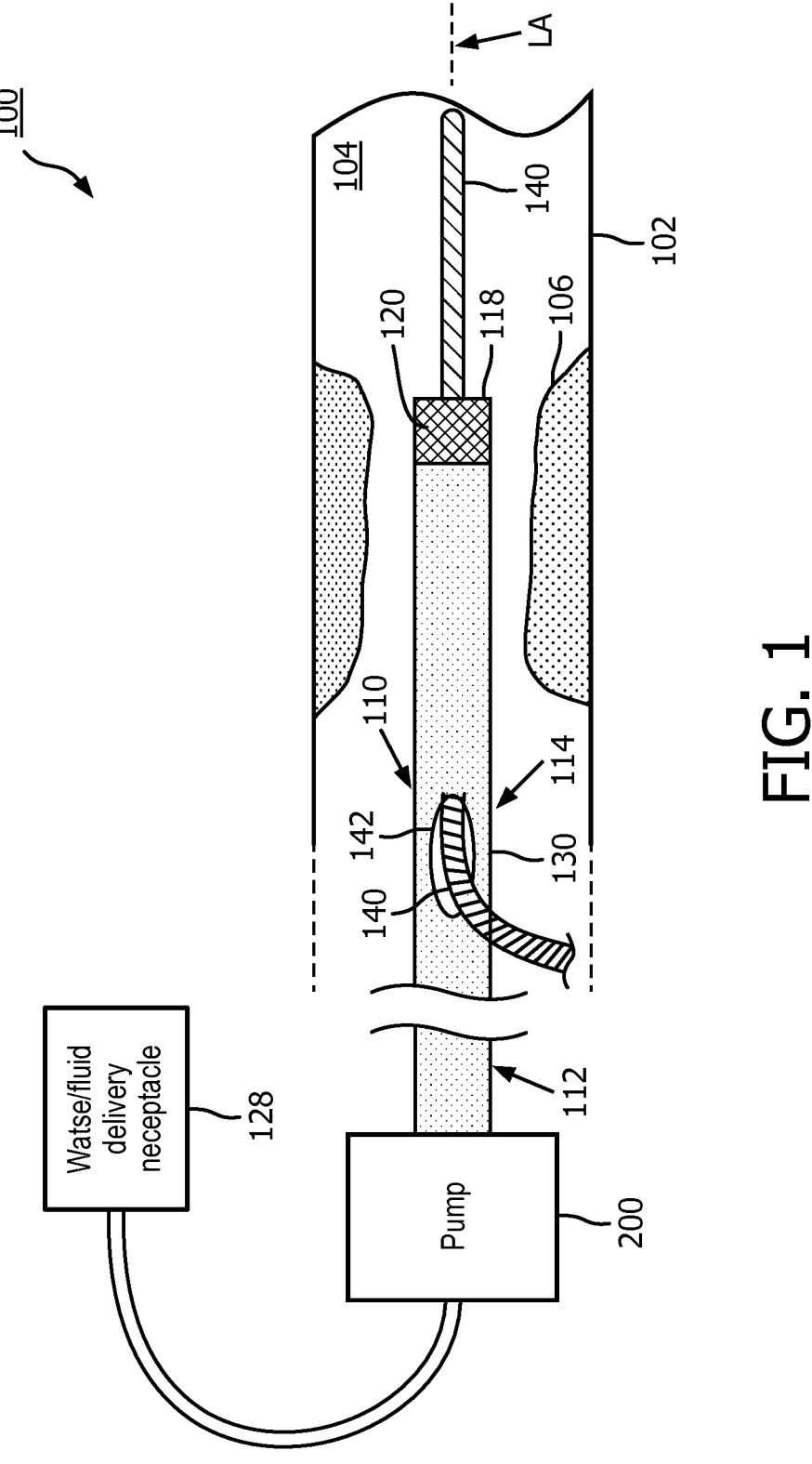
FIG. 1 is diagrammatic schematic view of a disposable pump system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Occasionally, biological material causing blockages or narrowing of blood vessels needs to be removed. The process of removing a blood clot, or thrombus, is referred to as a thrombectomy. One type of thrombectomy, known as aspiration, involves using suction with an intravascular catheter to remove the thrombus from the vessel. The aspiration is effectuated by a pump disposed outside the patient's body. Typically, pumps used in aspiration thrombectomy are large reusable units that must be sterilized between each use. Such pumps present significant upfront costs as well as ongoing maintenance costs. The present application presents hand-held and/or disposable pumps configured for use in aspiration thrombectomy that conserve size and weight and reduce cost while maintaining sufficiently high vacuum strength and functionality.

In some embodiments, thrombectomy pumps can be used in connection with intraluminal systems. FIG. 1 is a diagrammatic schematic view of an intraluminal therapeutic system 100, such as an aspiration thrombectomy system, according to some embodiments of the present disclosure. The system 100 can include an intraluminal device 110, a pump 200, and a receptacle 128. The intraluminal device 110 is structurally arranged (e.g., sized and/or shaped) to be positioned within anatomy 102 of a patient. The intraluminal device 110 aspirates biological material (e.g., occlusion 106) from within the anatomy 102 and applies ultrasound therapy to the anatomy 102.

Generally, the intraluminal device 110 can comprise a catheter, a guide catheter, and/or a guide wire. The intraluminal device 110 includes a flexible elongate member 130. As used herein, "elongate member" or "flexible elongate member" includes at least any thin, long, flexible structure structurally arranged (e.g., sized and/or shaped) to be positioned within a lumen 104 of the anatomy 102. For example, a distal portion 114 of the flexible elongate member 130 is positioned within the lumen 104, while a proximal portion 112 of the flexible elongate member 130 is positioned outside of the body of the patient. The flexible elongate member 130 can be used in conjunction with the pump 200 for aspiration thrombectomy. For example, the guidewire 140 can be retracted from the elongate member 130, and the pump 200 can be activated to create a vacuum or suction to aspirate fluid and/or biological material from the body lumen 104 and into the receptacle 128. The pump 200 (e.g., a pump chassis) is sized and shaped, structurally arranged, and/or otherwise configured to be manually supported by a user. For example, the pump 200 and/or the pump chassis is configured for sized and shaped, structurally arranged, and/or otherwise configured for handheld operation by a user, positioning on top of a patient bed, on a bedrail, etc.

The flexible elongate member 130 can include a longitudinal axis LA. In some instances, the longitudinal axis LA can be a central longitudinal axis of the flexible elongate member 130. In some embodiments, the flexible elongate member 130 can include one or more polymer/plastic layers formed of various grades of nylon, Pebax, polymer composites, polyimides, and/or Teflon. In some embodiments, the flexible elongate member 130 can include one or more layers of braided metallic and/or polymer strands. The braided layer(s) can be tightly or loosely braided in any suitable configuration, including any suitable per in count (pic). In some embodiments, the flexible elongate member 130 can include one or more metallic and/or polymer coils. All or a portion of the flexible elongate member 130 may have any suitable geometric cross-sectional profile (e.g., circular, oval, rectangular, square, elliptical, etc.) or non-geometric cross-sectional profile. For example, the flexible elongate member 130 can have a generally cylindrical profile with a circular cross-sectional profile that defines an outer diameter of the flexible elongate member 130. For example, the outer diameter of the flexible elongate member 130 can be any suitable value for positioning within the anatomy 102, including between approximately 1 Fr and approximately 15 Fr, including values such as 3.5 Fr, 5 Fr, 7 Fr, 8.2 Fr, 9 Fr, and/or other suitable values both larger and smaller.

The intraluminal device 110 includes or more lumens extending along all or a portion of the length of the flexible elongate member 130. The lumen of the intraluminal device 110 can be structurally arranged (e.g., sized and/or shaped) to receive and/or guide one or more other diagnostic and/or therapeutic instruments. The lumen(s) of the intraluminal device 110 may be centered or offset with respect to the cross-sectional profile of the device 110. In the illustrated embodiment, the intraluminal device 110 is a catheter and includes a guide wire lumen at the distal portion 114 of the flexible elongate member 130. A guide wire 140 extends through the guide wire lumen of the catheter 110 between an entry/exit port 142 and an exit/entry port at a distal end 118 of the flexible elongate member 130. Generally, the guide wire 140 is a thin, long, flexible structure that is structurally arranged (e.g., sized and/or shaped) to be disposed within the lumen 104 of the anatomy 102. During a therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more therapeutic instruments, including the intraluminal device 110, at the desired location within the anatomy 102. For example, the intraluminal device 110 moves through the lumen 104 of the anatomy 102 along the guide wire 140. In some embodiments, the lumen of the intraluminal device 110 can extend along the entire length of the flexible elongate member 130. In the illustrated embodiment, the exit/entry port 142 is positioned proximally of a therapeutic device 120 or component of the intraluminal device 110. In some embodiments, the exit/entry port 142, the exit/entry port at the distal end 118, and/or the lumen of the intraluminal device 110 is positioned distally of the device 120. In some embodiments, the intraluminal device 110 is not used with a guide wire, and the exit/entry port 142 can be omitted from the intraluminal device 110.

The anatomy 102 may represent any fluid-filled or surrounded structures, both natural and man-made. For example, the anatomy 102 can be within the body of a patient. Fluid can flow through the lumen 104 of the anatomy 102. The anatomy 102 can be a vessel, such as a blood vessel, in which blood flows through the lumen 104. In some instances, the intraluminal device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of a blood clot (thombus), plaque buildup, including without limitation plaque components such as fibrous, fibro-lipidic (fibro fatty), necrotic core, or calcified (dense calcium). In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The intraluminal device 110 may include a treatment device 120 at the distal portion 114 of the flexible elongate member 130. In some embodiments, the treatment device 120 is an artherectomy component, such as a blade. In some embodiments, the treatment device 120 is configured to apply an ultrasound therapy to the anatomy 102, such as the occlusion 106. For example, the treatment device 120 emits sound waves that damage the structure of the occlusion 106. In that regard, the device 110 and/or the treatment device 120 can be referenced as a thrombectomy device. The ultrasonic energy emitted by the treatment device 120 can create micro fractures in the occlusion 106. For example, the treatment device 120 can deliver ultrasonic energy in a targeted manner to cause cavitation (e.g., wave force cavitation, thermal cavitation, etc.) of the occlusion 106. Delivery of ultrasound therapy by the treatment device 120 advantageously facilitates thrombus dilution and/or vessel preparation. In some embodiments, the therapy device 120 is configured to deliver a pharmacological agent to the anatomy 102. The pharmacological agent can be a thrombolytic agent, a fibrinolytic agent, plasmin, plasmid, tissue plasminogen activator, urokinase, streptokinase, collagenace, hepranoid, anti-thrombin drug, any other suitable drug, and/or combinations thereof. Additional aspects regarding the intraluminal system 100, including the elongate member 130 and the therapy device 120, are described in U.S. Provisional App. No. 62/545,888, filed Aug. 15, 2017, U.S. Provisional Application No. 62/546,184, filed Aug. 16, 2017, and U.S. application Ser. No. 15/999,189, filed Aug. 15, 2018, each of which is hereby incorporated by reference.

Figure 2:
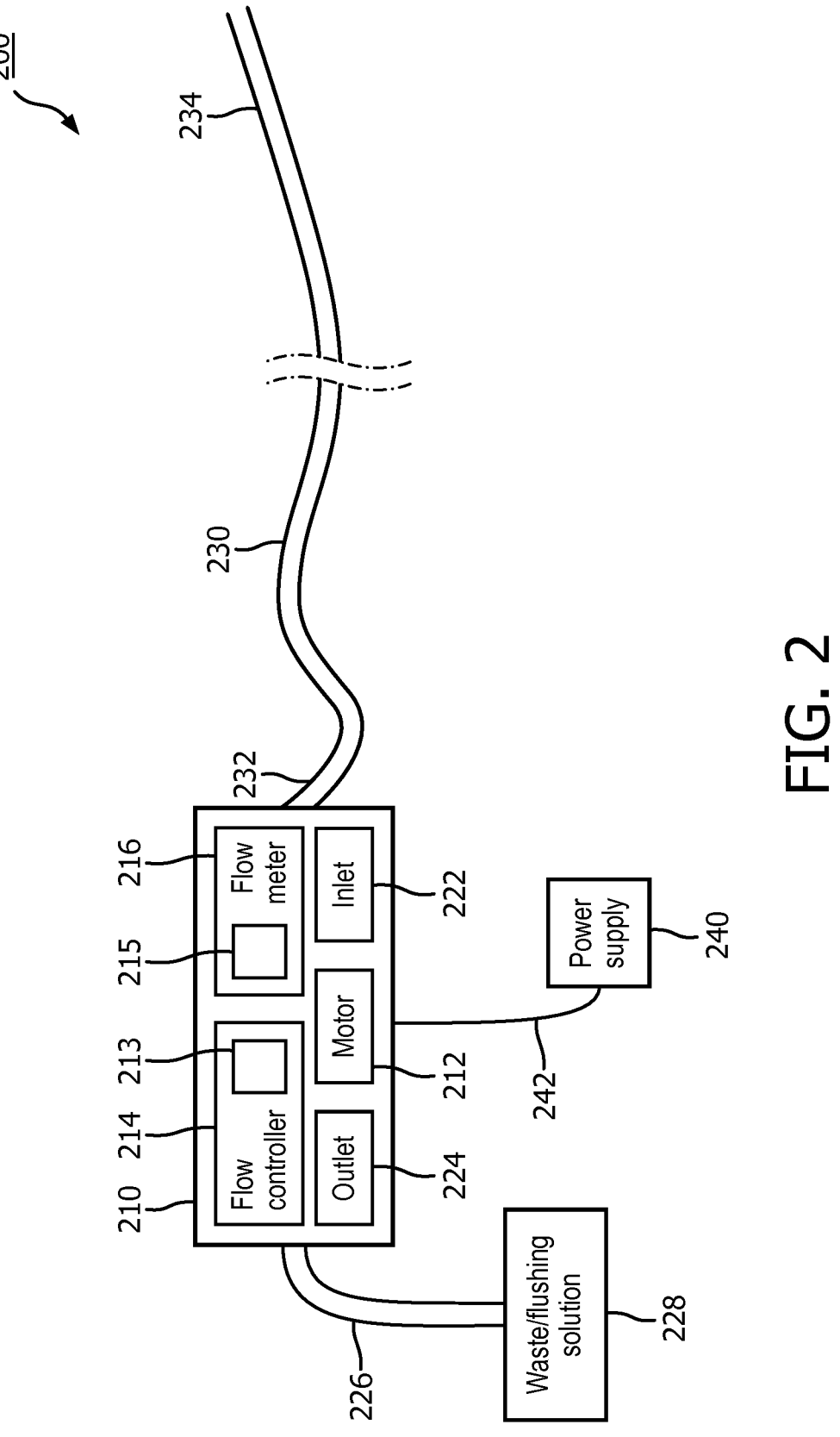
FIG. 2 is diagrammatic schematic view of disposable pump according to some embodiments of the present disclosure.

FIG. 2 is a diagrammatic schematic view of a disposable pump 200, according to an embodiment of the present disclosure. The pump 200 comprises a pump chassis 210, or pump body, that houses a motor or actuator 212, a flow controller 214, a flow meter 216, an inlet 222, and an outlet 224. The motor 212 is coupled to a power supply 240 via a power cable 242, and is configured to provide mechanical power (e.g., torque) to pump displacement mechanics, such as a piston, membrane, rotor, etc., to pump a fluid through the pump 200. In some embodiments, the power supply 240 is disposed within a separate housing than the pump chassis 210. In other embodiments, the power supply 240 is disposed within the pump chassis 210.

The flow meter 216 is configured to detect or measure a flow of fluid through the pump 200 and provide an indication of the flow. For example, in one embodiment, the flow meter 216 comprises a mechanical or analog gauge configured to measure a characteristic of fluid flow (e.g., fluid pressure) at one or more locations of the pump 200. In other embodiments, the flow meter 216 comprises an electronic flow meter, such as a digital flow meter configured to output an electrical signal indicating a value of a flow characteristic to another component (e.g., to the flow controller 214) and/or to output the measured flow value to a visual indicator 215, such as an on-board display. In some embodiments, the indicator 215 comprises an LED light or a speaker (i.e. an alarm) to indicate when the measured flow characteristic passes a threshold value.

The flow controller 214 comprises a mechanical valve or other suitable component for controlling a flow rate through the pump 200. In some embodiments, the flow controller 214 is electronically controlled by a processing component. The flow meter 216 can be communicatively coupled to the flow controller 214 to provide a feedback loop such that the flow controller 214 can dynamically adjust flow through the pump 200 in response to measured flow values provided by the flow meter 216. For example, during aspiration, a vacuum created by the pump 200 within the patient's vasculature may cause the vessel to collapse. The collapsing of the vessel would be detected by the flow meter 216 as a sudden decline in flow into the pump 200. In order to mitigate damage to the vessel, an electronic flow controller 214 can be configured to receive indications of the measured flow from the flow meter 216, and can accordingly adjust to restrict flow—and therefore decrease the suction—within the patient's vasculature to restore the shape and function of the vessel. In other embodiments, the flow meter 216 is in communication with the motor 212 to provide feedback directly to the motor 212, which can automatically adjust its output (e.g., speed, torque) depending on the measured flow. In still other embodiments, the flow controller 214 is manually controlled by a user. For example, the user may observe a flow characteristic measured and output by the flow meter 216, and manually adjust the flow controller 214 accordingly by using a mechanical or electronic input 213, such as a switch, button, lever, dial, knob, etc. In some embodiments, the flow controller is configured to repeatedly and/or rapidly open and close to generate pulses of fluid pressure (i.e., micro compression and expansion) that can assist to dislodge portions of a thrombus, or de-clog extracted material build-up within the intraluminal device 230. In still other embodiments, the motor 212 and/or pump displacement mechanics can be reversible to switch the pump direction, such as changing the pump from aspirating to injecting.

The chassis 210 comprises an inlet 222 at a distal portion of the pump 200 and an outlet 224 at a proximal portion of the pump 200. The inlet 222 is coupled to a disposable intraluminal device 230 to provide fluid communication between the patient's vessel and the pump 200. The intraluminal device 230 comprises a hollow elongate body having a proximal portion 232 and a distal portion 234. At least the distal portion 234 is configured to be inserted into the vasculature of the patient for aspiration. As explained further below, the intraluminal device 230 can comprise one or more lumens. For example, in some embodiments, the device 230 comprises an aspiration (or suction) lumen, a fluid delivery lumen, and/or a guidewire lumen. In some embodiments, the device 230 comprises a conduit or tubing, such as medical tubing, having one or more fluid-carrying lumens.

The proximal portion 232 of the intraluminal device 230 can connect to the inlet 222 of the pump 200 by, for example, a luer, a nozzle, a socket, or any other suitable connection and/or fitting configured to provide an adequate seal to maintain suction into the pump 200. In that regard, the proximal portion 232 of the intraluminal device 230 may fit directly into or over the inlet 222, which may comprise a socket or nozzle. In some embodiments, the inlet 222 is integrally formed with the pump chassis 210. In other embodiments, the inlet 222 is a separate component that is contained within and/or coupled to the pump chassis 210.

The outlet 224 of the pump is configured to direct aspirated fluid from the pump 200 into a receptacle 228. The outlet 224 is in fluid communication with the receptacle via an elongate member 226. The elongate member 226 may comprise a similar construction or configuration as the intraluminal device 230. The elongate member 226 may comprise a conduit or tubing having a lumen for carrying fluid. The outlet 224 may comprise a construction similar to that of the inlet 222. In other embodiments, the outlet 224 is in direct communication with the receptacle 228, without the need for tubing 226. For example, the outlet 224 may directly and sealably couple to the receptacle 228. The receptacle 228 comprises a waste container for receiving and containing the aspirated biological material. However, in some embodiments, the receptacle 228 comprises a reservoir that contains a fluid to be delivered to the patient's vessel, such as a saline fluid or a therapeutic agent.

The components of the pump 200 can comprise low weight and/or low-cost materials, such as plastic, consistent with a disposable design. For example, the pump chassis, inlet, outlet, and receptacle 228 can comprise materials such as nylon, Pebax, polymer composites, polyimides, and/or Teflon. In some embodiments, one or more pump components can comprise lightweight metals such as aluminium or stainless steel. The pump 200 can be configured to connect to or interface with existing intraluminal products, such as catheters, sheaths, and standard power supplies, in order to reduce overall cost of using the pump 200. The components of the pump 200 can include weight-reducing shapes, such as cut-outs to reduce overall weight of the pump 200. In some embodiments, the intraluminal device 230 and/or the pump 200 comprises one or more shutoff valves to prevent bleed out during attachment and removal of the intraluminal device 230 to the patient's vasculature. The chassis 210 can include waterproofing or sealing components and/or material, such as waterproof adhesives, O-rings, hydrophobic coatings or materials, or any other suitable waterproofing materials.

Figure 3:
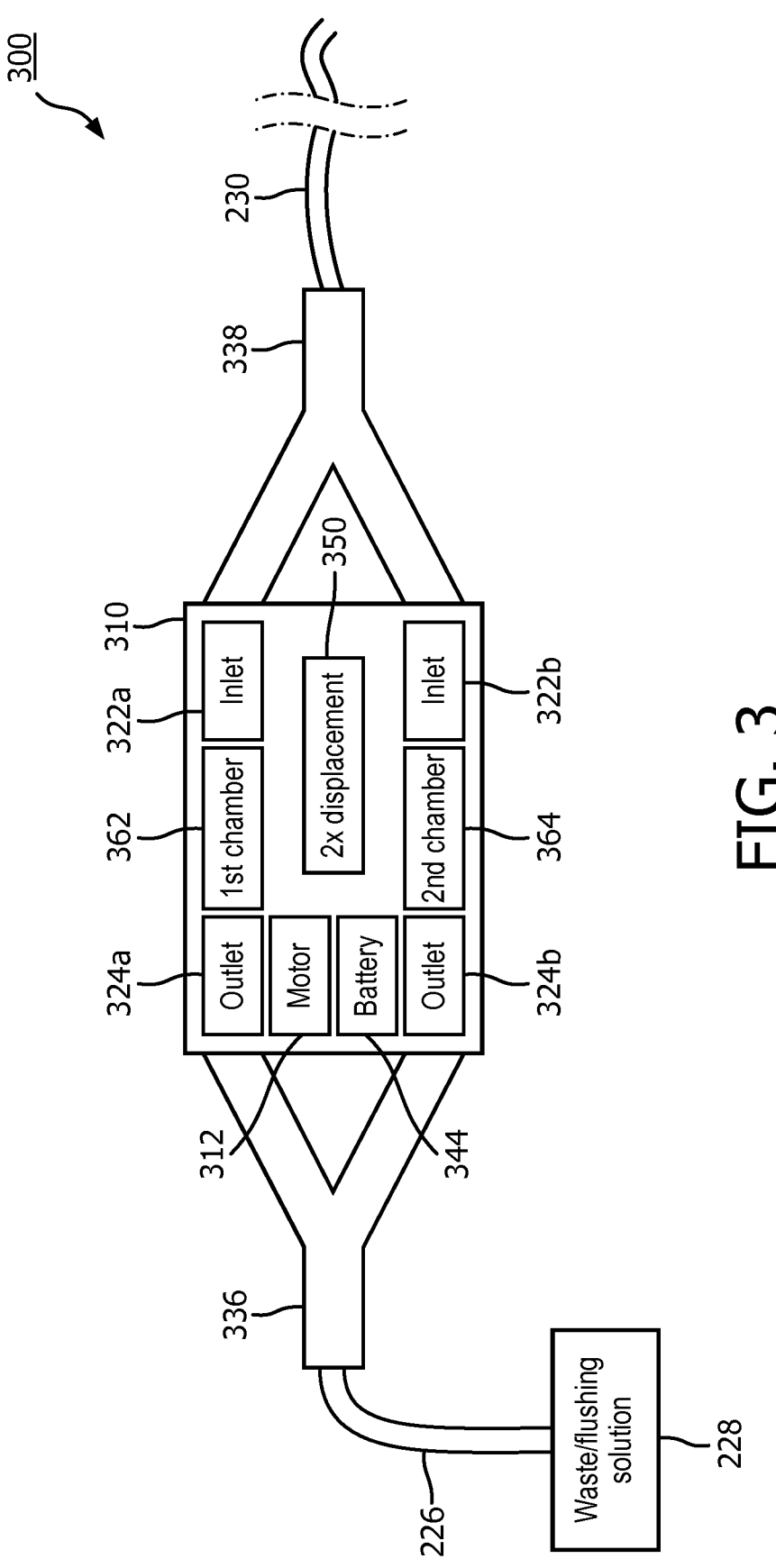
FIG. 3 is diagrammatic schematic view of a disposable pump according to some embodiments of the present disclosure.

FIG. 3 illustrates a disposable pump 300, according to another embodiment of the present disclosure. The pump 300 comprises many similar or identical components as the pump 200 shown in FIG. 2. For example, the pump 300 comprises a pump chassis 310 that houses a motor 312, inlets 322a, 322b, and outlets 324a, 324b. In the embodiment of FIG. 3, the pump comprises a first inlet 322a and a first outlet 324a in communication with a first chamber 362, and a second inlet 322b and second outlet 324b in communication with a second chamber 364. The first chamber 362 and second chamber 364 are separated from one another such that they are not in direct fluid communication with one another. As explained below, in some embodiments, each of the first chamber 362 and the second chamber 364, and their corresponding inlets and outlets, are used to aspirate fluid and biological material from a patient's vessel. In other embodiments, one chamber and its corresponding inlet and outlet is used to aspirate fluid from the vessel, while the other chamber and its corresponding inlet and outlet are used to pump a fluid to the vessel. A single motor 312 drives pumping through both chambers 362, 364. In that regard, the motor 312 is operatively coupled to a dual displacement adapter 350 that is configured to distribute power and/or torque from the motor 312 to each of the first chamber 362 and the second chamber 364. Because the motor 312 is one of the largest spatial constraints in designing a hand-held disposable pump, using the dual displacement adapter 350 can be advantageous because it can run two pump displacement systems with a single motor.

In some embodiments, the dual displacement adapter 350 is coupled to one or more pistons, rotors, propellers, or membranes in communication with the first and second chambers 362, 364 to create a pumping action through the chambers 362. In some embodiments, the dual displacement adapter 350 is constructed and/or configured to pump fluid through both of the chambers 362, 364 in the proximal direction to pump fluid and biological material from the patient's vessel through the disposable intraluminal device 230 and into the pump 300. In other embodiments, the dual displacement adapter and/or the chambers 362, 364 are configured to move fluids in opposing directions. For example, the first chamber 362 may be configured to pump a flushing fluid and/or therapeutic agent from a reservoir to the patient's vessel, while the second chamber 364 is configured to pump fluid from the patient's vessel into the waste receptacle 228.

The inlets 322a, 322b are connected to the intraluminal device 230 by a Y-luer 338. Depending on the configuration of the dual displacement adapter 350 and the pump chambers 362, 364, the Y-luer 338 may connect the inlets 322a and 322b into a single lumen or separate lumens (e.g., an aspiration lumen and a fluid delivery lumen). Similarly, the outlets 324a, 324b are connected to the receptacle 228 by a Y-luer 336. In some embodiments, the Y-luer joins the outlets 324a, 324b to a single lumen leading into the receptacle 228. In other embodiments, the Y-luer 336 connects the outlets 324a, 324b to separate lumens.

The pump 300 further comprises a battery 344 housed within the pump chassis 310. In some embodiments, the battery 344 is rechargeable and/or replaceable. In other embodiments, the battery 344 is not rechargeable and/or replaceable. Whether the pump 300 is powered by the battery 344 or an external power source, in some embodiments, the pump is configured to operate with an input voltage of between about 10V and about 20V. Although not shown in FIG. 3, the pump 300 may also comprise a flow meter and/or a flow controller in some embodiments. In some embodiments, the intraluminal device 230, the inlets 322, chambers 362, 364, outlets 324, and waste receptacle 228 are arranged in-line, in a straight orientation to maintain a direct draw within the disposable form factor of the pump 300.

Figure 4:
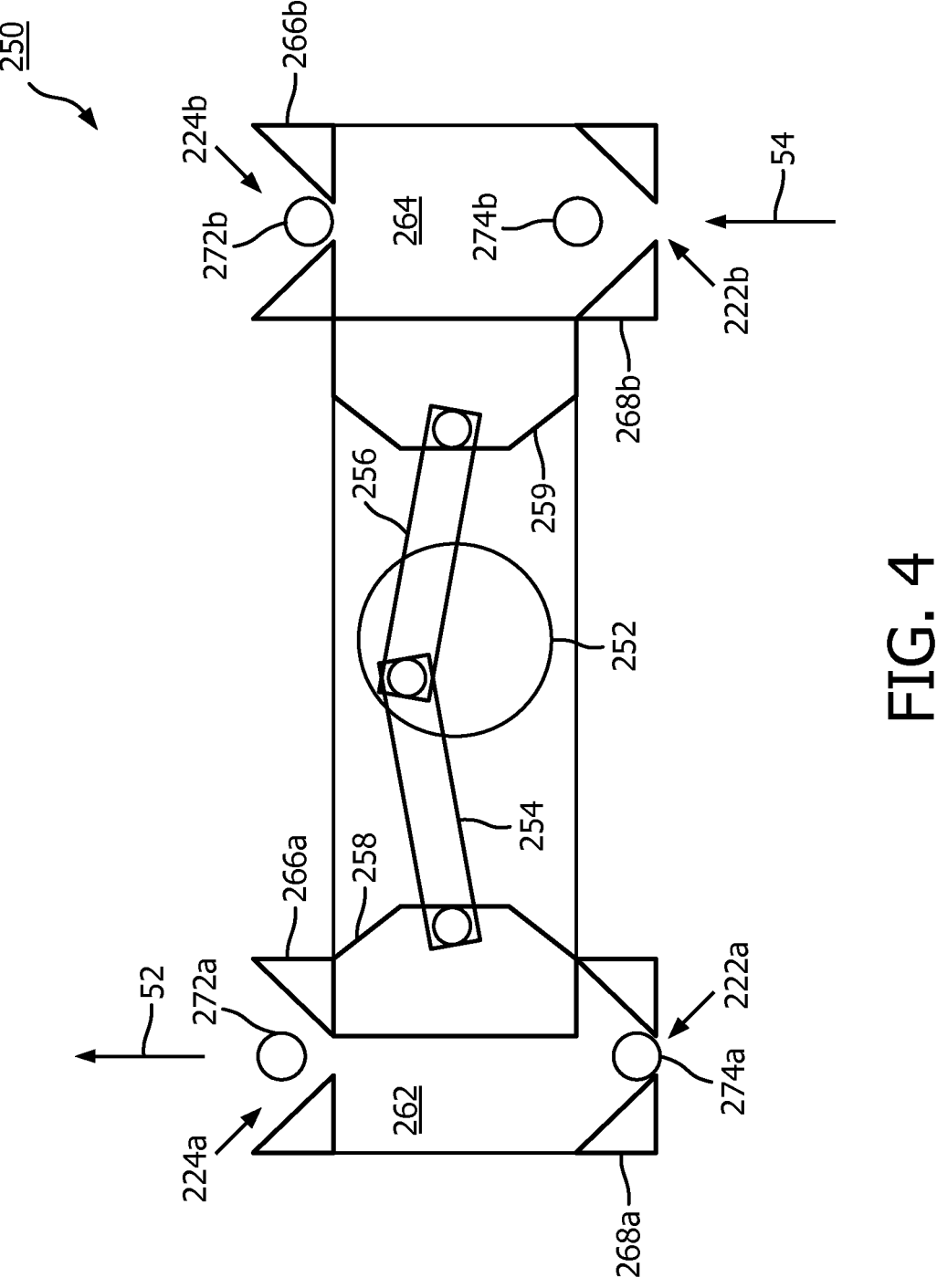
FIG. 4 is diagrammatic view of a dual displacement adapter of a disposable pump according to some embodiments of the present disclosure.

FIG. 4 is a diagrammatic schematic view of a dual displacement adapter 250, according to one embodiment of the present disclosure. The dual displacement adapter 250 of FIG. 4 comprises a cam 252 configured to couple to a motor, a first crankshaft 254 coupled to a first piston 258, and a second crankshaft 256 coupled to a second piston 259. As the motor rotates the cam 252, the crankshafts 254 and 256 advance and retract the pistons 258 and 259 in an oscillating fashion. When the pistons 258, 259 advance into the first and second pump chambers 262 and 264, respectively, the volume of the chambers decreases, which causes the first ball valve 272a to raise, allowing egress of fluid from within the chamber 262 out the first outlet 224, shown by the first fluid arrow 52, while a first inlet ball valve 274a remains closed. As the first piston 258 retracts from the first chamber 262, the first outlet ball valve 272a closes by falling back to the first outlet valve stop 266a. The drop in pressure also causes the first inlet ball valve 274a to rise away from the first outlet valve stop 268a to allow ingress of fluid through the first inlet 222*a*. The same process occurs in an alternate pattern with respect to the second chamber 264, second piston 259, second outlet 224*b* comprising second outlet ball valve 272*b* and second outlet valve stop 266*b*, and the second inlet 222*b* comprising the second inlet ball valve 274*b* and second inlet valve stop 268*b*. Fluid ingress into the second chamber 264 is shown by fluid arrow 54.

Because the pistons 258, 259 pump fluid through the chambers 262, 264 in an alternating fashion, the dual displacement adapter 250 may provide a more steady movement of fluids, which may correspond to a more steady fluid pressure within the vessel. In other embodiments, the directionality of one or both of the chambers 262, 264 can be changed by, for example, rotating the valve stops 180 degrees such that the inclined portions of the valve stops face toward the inlets 222*a*, 222*b*. Thus, in some embodiments, the dual displacement adapter 250 can provide enable both aspiration and fluid delivery from a single motor. In other embodiments, the pistons 258, 259 can be replaced by flexible membranes, and the cam 252 and crankshafts 254, 256 can be replaced with analogous components for a diaphragm-style pump. Furthermore, valves of the pump 200 and/or dual displacement adapter 250 can comprise other types of valves besides ball valves, such as leaf valves, or any other suitable valve. Although not specifically illustrated, other types of dual displacement adapters are contemplated by the present disclosure that can distribute mechanical power from a single motor or actuator to two or more pump-driving components.

Figure 5:
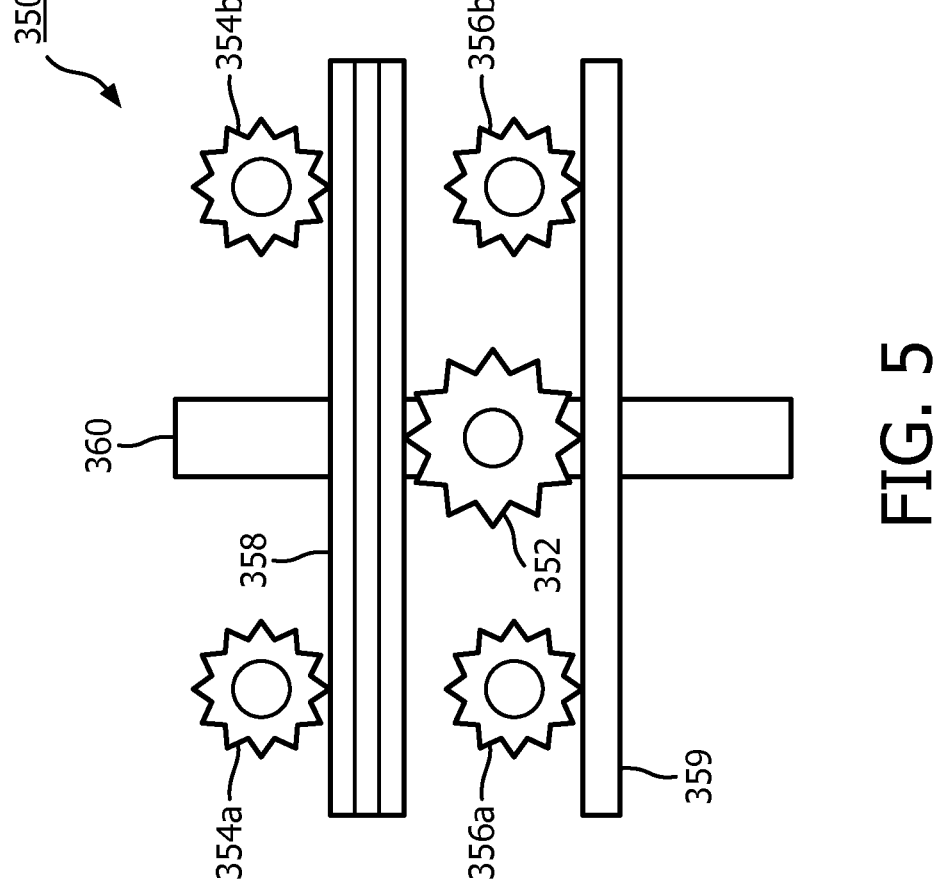
FIG. 5 is diagrammatic view of a dual displacement adapter of a disposable pump according to some embodiments of the present disclosure.

FIG. 5 shows a diagrammatic schematic view of a dual displacement adapter 350, according to another embodiment of the present disclosure. In the embodiment of FIG. 5, the dual displacement adapter 350 comprises a series of gears configured to distribute power or torque from a single motor to other pump components. The dual displacement adapter 350 comprises a drive gear 352 coupled to a motor, a dual bevel gear 358, a lower bevel gear 359, first and second top pinions 354*a*, 354*b*, and first and second bottom pinions 356*a*, 356*b*. The dual displacement adapter 350 can be coupled to a rotary pump. In that regard, the first top pinion 354*a* and first bottom pinion 356*a* can be coupled to a first rotary pump, and the second top pinion 354*b* and second bottom pinion 356*b* can be coupled to a second rotary pump. Each pinion can be coupled to a separate rotor of a rotary pump. In other embodiments, each pinion is in communication with a separate piston or membrane to drive fluid through a separate pump chamber.

Figure 6:
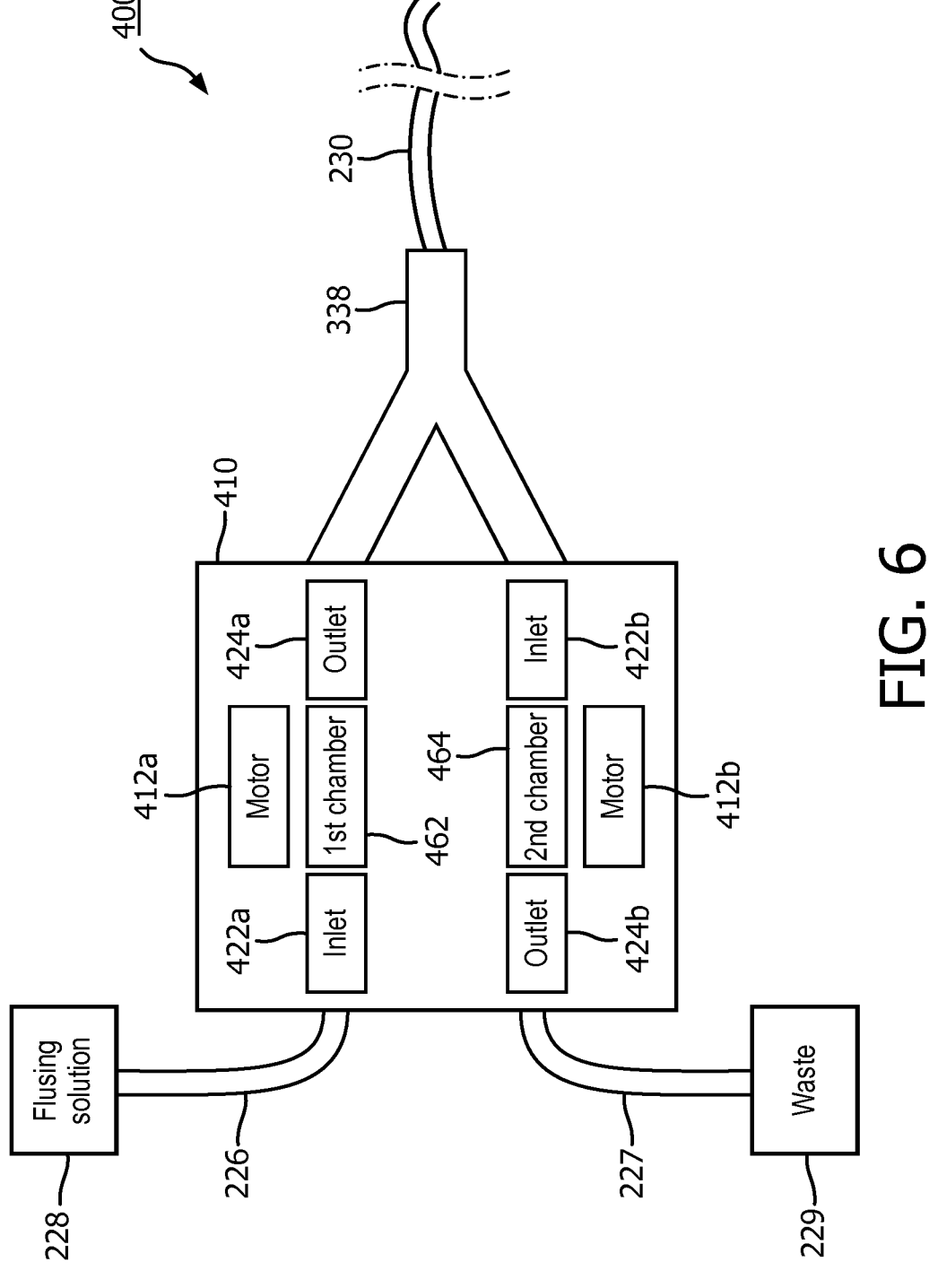
FIG. 6 is diagrammatic schematic view of a disposable pump according to some embodiments of the present disclosure.

FIG. 6 is a diagrammatic schematic view of a dual chamber disposable pump 400, according to an embodiment of the pleasant disclosure. Similar to the pump 300 shown in FIG. 3, the pump 400 of FIG. 6 includes a first chamber 462 in communication with a first inlet 422*a* and a first outlet 424*a*, and a second chamber 464 in communication with a second inlet 422*b* and a second outlet 424*b*. In contrast to the pump 300 of FIG. 3, the pump 400 of FIG. 6 includes a second motor 412*b* configured to drive the second chamber 464, while a first motor 412*a* is configured to drive the first chamber 462. Thus, the pump 400 of FIG. 6 does not require a dual displacement adapter to pump fluid through each chamber 462, 464.

The pump 400 is configured to deliver a flushing solution from a reservoir 228 to the vessel of the patient through the first chamber 462, and to aspirate fluid and biological material from the vessel of the patient to a waste receptacle 229 through the second chamber 464. The first inlet 422*a* is connected to the reservoir 228 of flushing fluid by a first tubular member 226, and the second outlet 424*b* is connected to the waste receptacle 229 through a second tubular member 227.

The first outlet 424*a* and second inlet 422*b* are connected to the intraluminal device 230 via the Y-luer 238. The Y-luer 238 joins each of the first outlet 424*a* and the second inlet 422*b* to separate lumens within the intraluminal device 230. In some embodiments, the separate lumens are coaxial. In other embodiments, the lumens are parallel and run side-by-side within the intraluminal device 230. In some embodiments, the Y-luer 238 comprises a shut-off valve at each fork of the Y-luer 238.

Figures 7A, 7B:
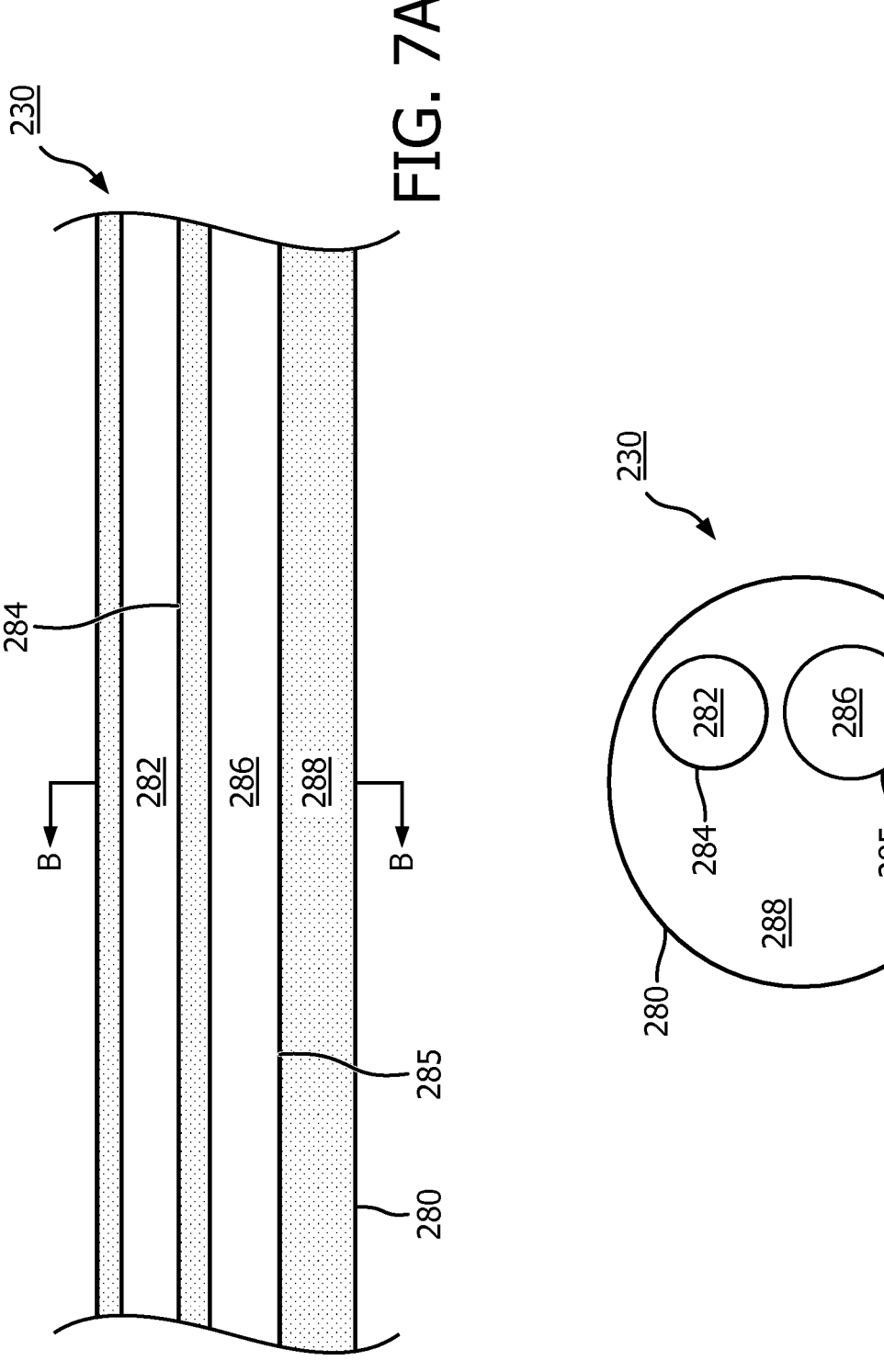
FIG. 7A is a schematic view of a disposable intraluminal device configured to be positioned within a lumen of a patient, according to embodiments of the present disclosure.
FIG. 7B is a schematic view of a disposable intraluminal device configured to be positioned within a lumen of a patient, according to embodiments of the present disclosure.

FIGS. 7A and 7B depict a disposable intraluminal device, according to one embodiment of the present disclosure. FIG. 7A is a diagrammatic side view of the intraluminal device 230, and FIG. 7B is a cross-sectional view taken along the line B-B, as shown in FIG. 7A. The intraluminal device 230 can be used with a dual chamber pump, such as the pump 400 of FIG. 6. The intraluminal device 230 comprises an outer sheath 280 that surrounds a guidewire lumen 288. Within the guidewire lumen 288 is a fluid delivery lumen 282 surrounded by a fluid delivery sheath 284 and an aspiration lumen 286 surrounded by an aspiration sheath 285. The guidewire lumen 288 is sized and shaped to allow a guidewire to pass therethrough.

In other embodiments, the intraluminal device 330 comprises only two lumens. For example, the aspiration lumen 286 or the fluid delivery lumen 282 can function as a guidewire lumen. In some embodiments, the fluid delivery lumen 282 and the aspiration lumen 286 are coaxial, such that the aspiration lumen is surrounded by the fluid delivery lumen, or vice versa.

Figure 8:
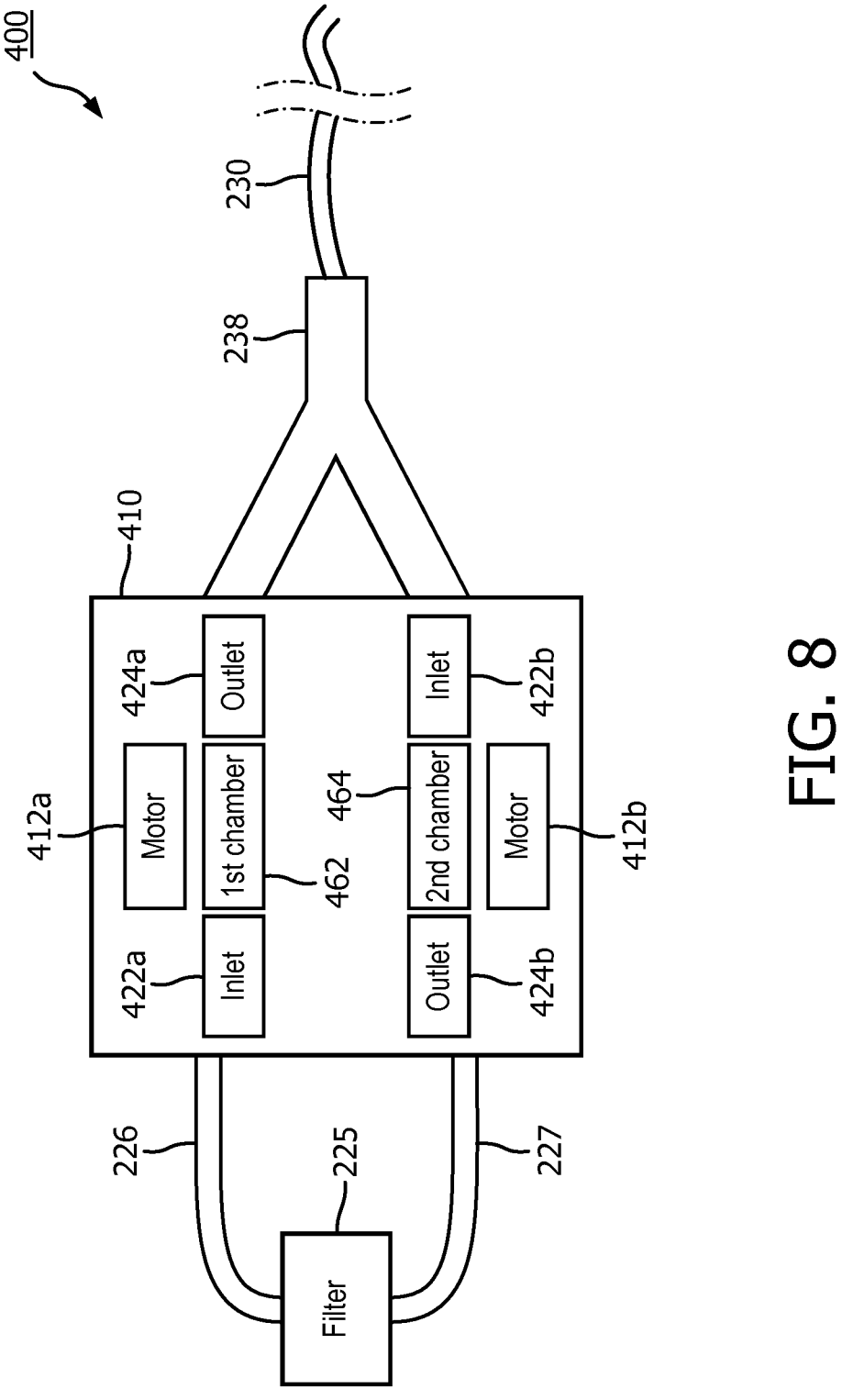
FIG. 8 is diagrammatic schematic view of a disposable pump according to some embodiments of the present disclosure.

FIG. 8 is a diagrammatic schematic view of the pump 400 shown in FIG. 6, according to another embodiment of the present disclosure. In FIG. 8, the pump 400 is configured to aspirate fluid and biological material through the second chamber 464, which expels the fluid and biological material through the second outlet 424*b* and the aspiration tubular member 227 to the filter 225. The filter 225 is configured to remove biological material or other foreign bodies from the aspirated fluid (e.g., blood), and recycle the filtered fluid through the fluid delivery tubular member 226 and the first inlet 422*a*, where it is pumped in the first chamber 462 through the first outlet 424*a* and intraluminal device 230 back into the patient's vessel. The filter 225 can comprise a mesh of stainless steel, ePTFE strands, or any other biologically suitable material. The mesh size of the filter 225 can be configured to remove symptomatic emboli from the extracted fluid. In some embodiments, the filter comprises a portion of tubing with a filter mesh disposed within the tubing, which can attach to the inlets and/or outlets of the pump 400 by conventional means.

Figure 9:
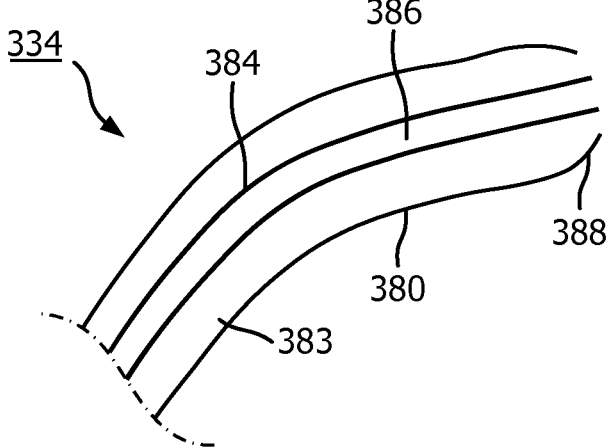
FIG. 9 is a diagrammatic schematic view of a distal portion of an intraluminal device, according to one embodiment of the present disclosure.
Figure 10:
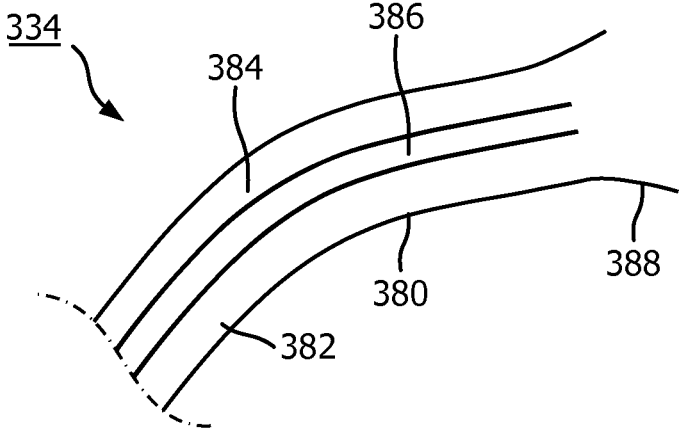
FIG. 10 is a diagrammatic schematic view of a distal portion of an intraluminal device, according to one embodiment of the present disclosure.
Figure 11:
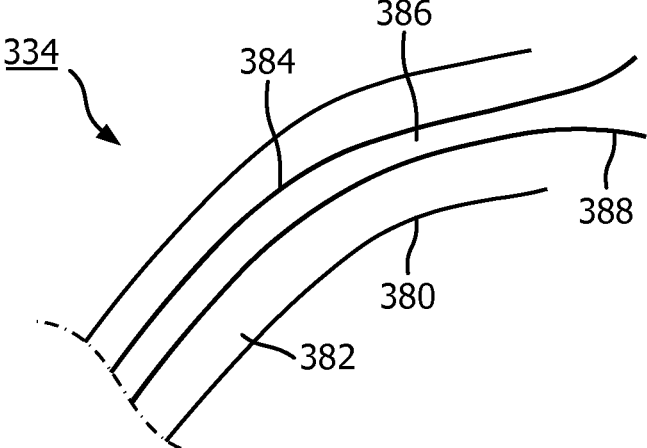
FIG. 11 is a diagrammatic schematic view of a distal portion of an intraluminal device, according to one embodiment of the present disclosure.

FIGS. 9, 10, and 11 depict various configurations of a distal portion 334 of an intraluminal device, according some embodiments of the present disclosure. In the embodiments of FIGS. 9, 10, and 11, an aspiration lumen 386 is coaxial with a fluid delivery lumen 383, both of which are disposed within a sheath 380. The distal portion 334 comprises a distal tip 388 that can be shaped and/or configured to exhibit various qualities. For example, in FIG. 9, the tip 388 comprises a narrowing taper of the sheath 380. The narrowing taper of the tip 388 focuses or directs a flushing fluid and/or therapeutic agent to the desired location. In FIG. 10, the distal tip comprises a widening taper of the sheath 380. The widening taper may provide for a wider stream of fluid to pass through the fluid delivery lumen 382, and may serve to restrict biological material from passing around the lumens 382, 386. The taper of the sheath 380 extends distally of the aspiration sheath 384. In FIG. 11, the distal tip 388 comprises a widening taper of the aspiration sheath 384. The widening taper of the aspiration sheath 384 may serve to create a wider stream of fluid and biological material aspirated into the aspiration lumen 386. The aspiration sheath 384 extends distally of the sheath 380 to place the aspirating distal tip 388 distal of the fluid delivery lumen 382.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal system for aspirating biological material from a lumen of a patient, comprising:
   a disposable intraluminal device comprising a distal portion configured to be positioned within the lumen of the patient and a proximal portion in fluid communication with the distal portion and positioned outside of the patient; and
   a disposable pump configured to aspirate the biological material from the lumen of the patient, the disposable pump coupled to the proximal portion of the intraluminal device and comprising a pump chassis that houses:
      an inlet port configured to sealably attach to the proximal portion of the intraluminal device;
      an outlet port configured to expel the aspirated biological from the pump;
   a flow controller configured to adjust a fluid flow through the pump;
   an actuator;
      a first pump chamber;
      a second pump chamber separate from the first pump chamber; and
      a dual displacement adapter coupled to the actuator such that the actuator is configured to drive the dual displacement adapter to pump fluid through each of the first pump chamber and the second pump chamber in an alternating fashion, and
   wherein the pump chassis is sized and shaped to be manually supported by a user.

2. The intraluminal system of claim 1, wherein the flow controller comprises a mechanical valve that is manually controllable by the user.

3. The intraluminal system of claim 1, wherein the pump chassis further houses a flow meter configured to detect a fluid flow through the pump and to provide an indication of the fluid flow, and wherein the flow controller comprises an electronic flow control device.

4. The intraluminal system of claim 3, wherein the flow meter comprises an electronic flow meter, and wherein the flow meter is in communication with the flow controller to provide feedback to the flow controller.

5. The intraluminal system of claim 4, wherein the flow meter and flow controller are configured to operate in a proportional-integral-derivative arrangement.

6. The intraluminal system of claim 3, wherein the flow controller is configured to repeatedly open and close to generate pulses of fluid pressure within the lumen of the patient.

7. The intraluminal system of claim 1,
   wherein the disposable intraluminal device comprises a fluid delivery lumen and an aspiration lumen separate from the fluid delivery lumen, and wherein the pump chassis further houses:
   a distal outlet in communication with the fluid delivery lumen of the disposable intraluminal device and the first pump chamber; and
   a distal inlet in communication with the aspiration lumen of the disposable intraluminal device and the second pump chamber,
   a proximal inlet in communication with the first pump chamber; and
   a proximal outlet in communication with the second pump chamber,
      wherein the pump is configured to pump a fluid from a fluid source coupled to the proximal inlet to the lumen of the patient through the first pump chamber, and wherein the pump is configured to aspirate the biological material from the lumen of the patient through the second pump chamber.

* * * * *